United States Patent [19]

Ueno et al.

[11] Patent Number: 5,362,751
[45] Date of Patent: Nov. 8, 1994

[54] TRACHEOBRONCHODILATOR USING 16-SUBSTITUTED PGES

[75] Inventors: Ryuzo Ueno; Ryuji Ueno, both of Nishinomiya; Tomio Oda, Sanda, all of Japan

[73] Assignee: Kabushiki Kaisha Ueno Seiyaku Oyo Kenkyujo, Osaka, Japan

[21] Appl. No.: 77,495

[22] Filed: Jun. 17, 1993

Related U.S. Application Data

[63] Continuation of Ser. No. 744,682, Aug. 9, 1991, abandoned, which is a continuation of Ser. No. 349,475, May 9, 1989, abandoned.

[30] Foreign Application Priority Data

May 11, 1988 [JP] Japan .................................. 63-115409

[51] Int. Cl.$^5$ .................... A61K 31/215; A61K 31/20
[52] U.S. Cl. ................... 514/530; 514/559; 514/558; 514/560
[58] Field of Search ............... 514/530, 559, 560, 558

[56] References Cited

U.S. PATENT DOCUMENTS

| 491,711 | 3/1876 | Kao et al. | 260/240 R |
| 4,022,821 | 5/1977 | Strike | 260/514 D |
| 4,038,308 | 7/1977 | Strike | 260/514 D |

FOREIGN PATENT DOCUMENTS 0153858 9/1985 European Pat. Off. .

OTHER PUBLICATIONS

Chemical Abstracts, vol. 74, 1971, p. 78, Abstract 120819y.
J. Pharm. Pharmac., vol. 29, May 10, 1977, pp. 752–755.
Br. J. Pharmac., vol. 54, 1975, pp. 397–399, Crutchley, et al.
Journal of Pharmacology and Experimental Therapeutics, vol. 178, No. 3, 1971.
Journal of Pharmacology and Experimental Therapeutics, vol. 214, No. 1, 1979.
Journal of Pharmacology and Experimental Therapeutics, vol. 247, No. 2, 1988.

*Primary Examiner*—Marianne M. Cintins
*Assistant Examiner*—T. J. Criares
*Attorney, Agent, or Firm*—Sughrue, Mion, Zinn, Macpeak & Seas

[57] ABSTRACT

The present invention provides a tracheobronchodilator comprising 15-keto-PGEs, reduced in stimuli against bronchi and other side effects.

21 Claims, No Drawings

TRACHEOBRONCHODILATOR USING 16-SUBSTITUTED PGES

This is a continuation of application Ser. No. 07/744,682 filed Aug. 9, 1991, now abandoned, which is a continuation of application Ser. No. 07/349,475 filed May 9, 1989, now abandoned.

BACKGROUND OF THE INVENTION

The present invention relates to a tracheobronchodilator containing 15-keto-prostaglandin E and their derivatives. In the present specification a series of prostaglandins and their derivatives is abbreviated to PGs. Accordingly, a series of compounds belonging to 15-keto-prostaglandin E such as 15-keto-prostaglandin $E_1$, $E_2$, esters, salts, or others having substituents is generically called 15-keto-PGEs. Term "$PGE_1s$" means a series of compounds belonging to $PGE_1$.

Prostaglandin is a generic name of one kind of carboxylic acids having a variety of physiological activities, which are found in tissues or internal organs of humans or animals. PGs have a basic skeleton of a prostanoic acid represented by following formula:

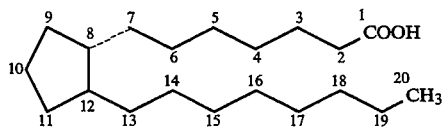

There have been provided various kinds of synthetic PGs modified on one or more carbon atom(s) of the skeleton.

PGs are classified into PGAs, PGBs, PGCs, PGDs, PGEs, PGFs, PGIs, and PGJs and so on according to the structure of the five members ring in the above skeleton. Further, they are classified into $PG_1s$ in which the bond between 5- and 6-positions is a single bond; $PG_2s$ in which the bond between 5- and 6-positions is a double bond; and $PG_3s$ in which the bonds between 5- and 6-positions, and between 17- and 18-positions are double bonds respectively. These PGs have a double bond between 13- and 14-position and a hydroxyl group on 15-position.

PGs exhibit various kinds of pharmacological and physiological activity. For instance, it has been known that $PGE_1s$, $PGE_2s$ and the like have a tracheobronchodilation which also have side effects such as enterocontraction, intraocular hypertension, and especially stimuli against bronchi.

There have been also found of PGEs in metabolites of animals or humans, in which the bond between 13- and 14-positions is a single bond (saturated) and the carbon atom of 15-position forms a carbonyl group; or in which the bond between 13- and 14-positions is a double bond and the carbon atom of 15-position constitutes a carbonyl group.

15-keto-prostaglandin E (noted as 15-keto-PGE hereinafter) and 13,14-dihydro-15-keto-prostaglandin E (noted as 13,14-dihydro-15-keto-PGE hereinafter) are known as a substance naturally produced by an enzyme in the metabolism of prostaglandin E (noted as PGE hereinafter) in a living body. These 15-keto-PGE have been considered to be physiologically and pharmacologically inactive substances (Acta Physiologica Scandinavica, Vol. 66, pp509 (1966)). It has never been recognized that these 15-keto-PGE have tracheobronchodilation activity.

SUMMARY OF THE INVENTION

It has been found that some kinds of metabolites of PGs exhibit activity of tracheaectasy and/or bronchoectasy (referred to as tracheobronchodilation hereinafter). Further, strengthened tracheobronchodilation activity is found in the ester or salt of PGs metabolites or derivatives such as one having a double bond between 2- and 3-positions, one having a triple bond between 5- and 6-positions, one having one or more substituent(s) on 3-, 6-, 16-, 17-, 19- and/or 20-position(s), and one having a lower alkyl group or a hydroxyalkyl group on 11-position instead of the hydroxyl group.

The present invention provides a tracheobronchodilator containing 15-keto-PGEs in an effective amount for tracheobronchodilation and physiologically acceptable carriers.

According to the present invention there is provided a tracheobronchodilator strengthen in the activity of tracheobronchodilation in comparison with a natural PGEs, and reduced in the stimuli against bronchi or other side effects.

DETAILED DESCRIPTION OF THE INVENTION

The present invention provides a tracheobronchodilator containing 15-keto-PGEs in an effective amount for tracheobrenchodilation and physiologically acceptable carriers.

In the present specification 15-keto-PGEs are expressed according to the following nomenclature. The 15-keto-PGEs have a following basic structure:

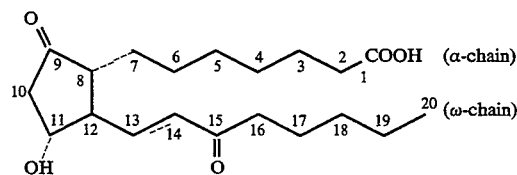

and the position number of carbon atom constituting α-chain, ω-chain and five members ring in the prostaglandin skeleton structure is used as it is in the nomenclature. That is, the position number of the carbon atom in the skeleton structure is started from the carbon atom constituting carboxylic acid of the terminal position of α-chain through the five members ring to ω-chain i.e. 1 to 7 are attached to the carbon atoms in the a-chain in this order, 8–12 are attached to the carbon atoms in the five members ring, and 13–20 are attached to the carbon atoms in the ω-chain. In the compound whose carbon number in a α-chain is less than 7 the position number is simply eliminated from 2 to 7 in this order without any change of the position number of the other carbons. In other word 15-keto-PGEs having 6 carbon atoms in the α-chain have no position of 2, i.e. 15-keto-PGEs of such compound are not renamed as 14-keto-PGEs. In case that carbon atoms increase in the α-chain, the carbon chain increased is nominated as a substituent on the carbon of position number 2 without any change of the position number of the other carbons. Therefore, 15-keto-PGEs having 8 carbon atoms in the α-chain are nominated as 15-keto-2-dicarboxy-2-acetic acid-PGEs. In case that the number of the carbon in the ω-chain decreases the position number is nominated as reducing it from the carbon of position number 20 (referred to as 20-position hereinafter, and similarly referred to other positions) one by one. In case the number of the carbon atoms in the ω-chain increases, the increased carbon chain is nominated as a substituent on 20-position. That is, 15-keto-PGEs having 10 carbon atoms in the ω-chain is nominated as 15-keto-20-ethyl-PGEs.

The above formula expresses a specific configuration which is most typical one, and in this specification compounds having such a configuration are expressed without any descriptions about it.

PGEs have a hydroxy group on the carbon atom of 11-position in general, but in the present specification term "PGEs" includes prostaglandins having other group instead of said hydroxyl group of normal PGE. Such PGEs are called as 11-dehydroxy-11-substituent-PGEs, for instance, 11-dehydroxy-11-methyl-PGEs in case of the substituent being a methyl group.

PGEs are classified to $PGE_1$ and $PGE_2$ according to the bonds between 5- and 6-positions.

$PGE_1$ and its derivatives (referred to as $PGE_1$s hereinafter) are nominated to a group of compounds in which the bonds between 5- and 6-positions is single bond. $PGE_2$ and its derivatives (referred to as $PGE_2$s hereinafter) are called to a group of compounds in which the bond between 5- and 6-positions is a cis-double bond. Therefore, PGEs having a structure of

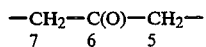

is nominated as 6-keto-$PGE_1$s, and PGEs having a structure of

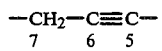

is called as 5,6-dehydro-$PGE_2$s.

15-keto-PGEs according to the present invention includes not restrictively:
13,14-dihydro-15-keto-$PGE_1$s and their derivatives,
13,14-dihydro-15-keto-$PGE_2$s and their derivatives,
13,14-dihydro-15-keto-$PGE_3$s and their derivatives,
15-keto-$PGE_1$s and their derivatives,
15-keto-$PGE_2$s and their derivatives,
15-keto-$PGE_3$s and their derivatives.

The tracheobronchodilation is remarkably expressed in 15-keto-PGEs esters represented by the following formula:

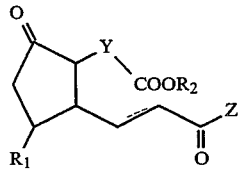

wherein $R_1$ is a hydroxyl group, a hydroxyalkyl group, or an alkyl group; Y is a saturated or unsaturated hydrocarbon moiety having 2–6 carbon atoms wherein a portion of carbon atoms constituting the hydrocarbon moiety may be carbonyl or a portion of hydrogen atoms constituting the hydrocarbon moiety may be substituted with other atoms or groups; Z is a saturated or an unsaturated hydrocarbon moiety which may constitute a straight chain or a ring, wherein a portion of hydrogen atoms of the hydrocarbon moiety may be substituted with one or more other atom(s) or group(s); $R_2$ is a hydrogen atom, a physiologically acceptable salt or ester residue.

Y which represents a saturated or an unsaturated hydrocarbon moiety having 2–6 carbon atoms includes an aliphatic hydrocarbon such as an alkylene group, an alkenylene group, an alkynylene group and the like. Y may preferably be a hydrocarbon chain having 6 carbon atoms.

Examples of PGEs of which Y is an unsaturated hydrocarbon moiety are $PGE_2$s, 5,6-dehydro-$PGE_2$s, PGEs of which the bond between 2- and 3-positions is unsaturated, and the like.

A portion of carbon atoms constituting hydrocarbon moiety represented by Y may be carbonyl, whose typical examples are 6-keto-$PGE_1$s in which the carbon atom of 6-position is carbonyl.

The hydrocarbon moiety represented by Y may be substituted with one or more other atom(s) or group(s), for example, halogen atoms such as a fluorine atom, a chlorine atom, typically a fluorine atom; an alkyl group such as methyl, ethyl; a hydroxyl group and the like. Typical examples of such substituents are 15-keto-PGEs having one or more alkyl group(s) on the carbon atom of 3-position.

Z represents a saturated or an unsaturated hydrocarbon moiety having 1–10 carbon atoms. The hydrocarbon moiety may be an aliphatic hydrocarbon or a cyclic hydrocarbon itself or in part. The hydrocarbon moiety represented by Z may be substituted with one or more other atom(s) or group(s).

The number of the carbon atoms of Z is preferably 3–7 in the straight chain. PGEs in which carbon numbers of Z are 5 are typical PGs. Therefore, the PGEs in which carbon numbers of the hydrocarbon moiety represented by Z are 6 or more than 6 are nominated as PGEs having a substituent on the carbon atom of 20-position. That is, PGEs in which the number of carbon atoms of Z is 6 are nominated as 20-methyl-PGEs.

Though the hydrocarbon moiety represented by Z may have one or more unsaturated bond(s) at any position, a saturated hydrocarbon is more preferable. Examples of the hydrocarbon moiety having a cyclic ring are a cyclopentyl or a cyclohexyl containing a carbon atom itself of 16- or 17-position as a ring constituting member.

The hydrocarbon moiety represented by Z may be substituted with one or more other atom(s) or group(s), for example, a halogen atom such as a fluorine atom or a chlorine atom; an alkyl group such as methyl, ethyl, isopropyl, isopropenyl; an alkoxy group such as methoxy, ethoxy; a hydroxyl group; a phenyl group; a phenoxy group and the like. The substituent(s) may be preferably located at the 16-, 17-, 19- and/or 20-position, but not restricted. Examples of preferable compounds include those having one or two, different or identical atom(s) and/or groups, for example, a halogen atom such as a fluorine atom; an alkyl group such as a methyl, ethyl group; an aromatic group such as phenyl, benzyl, phenoxy, which may have substituents, or hydroxyl or other group on 16-position. Other examples of preferable compounds include those having a cycloalkyl group such as a cyclopentyl or cyclohexyl group which contains the carbon atom of 16-position as a constituent of the cyclic ring; an alkyl group such as methyl, ethyl and the like on 17- or 19-position; an alkyl group such as methyl, ethyl, isopropyl, isopropenyl and the like; an alkoxy group such as methoxy, ethoxy, propoxy and the like on 20-position.

A generic name of PGEs is used to compounds having a prostanoic acid structure in which the carbon atom of 11-position has a hydroxyl group, and the carbon atom of 9-position forms a carbonyl group. In the present specification a prostanoic acid compound in which the hydroxyl group on 11-position is substituted with a hydroxyalkyl group or an alkyl group is also called as PGEs. Therefore, the 15-keto-PGEs of the present invention include compounds in which $R_1$ of the general formula (I) represents a hydroxyalkyl group or an alkyl group, for example, as a hydroxyalkyl group hydroxymethyl, 1-hydroxyethyl, 2-hydroxyethyl and 1-methyl-1-hydroxyethyl groups; as an alkyl group, methyl and ethyl groups are preferably exemplified.

The steric configuration of $R_1$ with respect to the carbon of 11-position may be $\alpha$, $\beta$ or mixture thereof.

Furthermore, examples of the PGEs included in the present invention are 13,14-dihydro compounds which are saturated at the 13- and 14-positions, and rather more preferable effects can be achieved from such 3,14-dihydro compounds.

15-keto-PGEs of the present invention may include various kinds of isomers such as tautomeric isomers, optical isomers, geometric isomers and the like. As an example of such isomers there is exemplified a tautomeric isomer between the hydroxyl group on 11-position and the carbonyl group of 15-position of 15-keto-PGEs. The latter tautomeric isomer is liable to be caused in 15-keto-PGEs having an electron withdrawing group such as fluorine atom on 16-position.

A hemiacetal, a tautomeric isomer between the hydroxyl group on 11-position and the carbonyl group of 15-position, may be sometimes formed, and an equilibrium mixture of the compound of R being a hydroxyl group and a hemiacetal may be given. Such an equilibrium mixture or a tautomeric isomer is also included in the 15-keto-PGEs of the present invention.

An equilibrium mixture of the isomers such as racemic or equilibrium mixture between a hydroxyl group and a hemiacetal in tautomerism also exhibits similar effects to a single compound.

Most preferable 15-keto-PGEs according to the present invention are PGEs of which 13- and 14-positions are saturated and the carbon atom of 15-position constitutes a carbonyl group, but 15-keto-PGEs of which the carbon atom of the 15-position simply constitutes carbonyl group are, of course, interest.

As 15-keto-PGEs exhibit strong activity of tracheobronchodilation, these 15-keto-PGEs are expected as a tracheobronchodilator, and due to such an activity they can be used as bronchial asthematics or medicines for patients who suffer from the increase of airway resistance.

The 15-keto-PGEs of the present invention may be a free acid, a physiologically acceptable salt or an ester.

As a salt there are exemplified, alkaline metal salts such as sodium salt, potassium salt and the like; alkaline earth metal salts such as calcium salt, magnesium salt, and the like; ammonium salts; physiologically acceptable amine salts such as monomethylamine salt, dimethylamine salt, cyclopentylamine salt, benzylamine salt, piperidine salt, tromethamine salt, monoethanolamine salt, diethanolamine salt, monomethylmonoethanolamine salt, lysine salt, tetraalkylammonium salt and the like.

Useful ester ($R_2$) of 15-keto-PGEs may include a saturated or an unsaturated lower alkyl ester which may have a branched chain such as methyl, ethyl, propyl, n-butyl, isopropyl, t-butyl, 2-ethylhexyl, allyl and the like; an aliphatic cyclic ester such as cyclopropyl, cyclopentyl, cyclohexyl and the like; an aromatic ester such as benzyl, phenyl and the like, which may have substituents; a hydroxyalkyl or an alkoxyalkyl ester such as hydroxyethyl, hydroxyisopropyl, hydroxypropyl, polyhydroxyethyl, polyhydroxyisopropyl, methoxyethyl, ethoxyethyl, methoxyisopropyl and the like; a trialkylsilyl ester such as trimethylsilyl, triethylsilyl and the like; a heterocyclic ester such as tetrahydropyranyl and the like. Preferable esters for the present invention are a lower alkyl ester which may have a branched chain, for instance, methyl, ethyl, propyl, n-butyl, isopropyl, t-butyl; a benzyl ester; a hydroxyalkyl ester such as hydroxyethyl, hydroxy isopropyl; and the like.

The activity of the tracheobronchodilation can be exhibited in any 15-keto-PGEs in which the carboxyl group of $\alpha$-chain is free, esterified or salts forms, but particularly strongly exhibited in the compounds of which the bond between 2- and 3-positions is a double bond, the bond between 5- and 6-positions is a triple bond, or having one or more substituent(s) on 3-, 6-, 16-, 17-, 19- and/or 20-position.

Preferable substituents which may be attached to one or more carbon atom(s) of 3-, 17- and/or 19-position are $C_1$-$C_4$ alkyl groups, especially methyl group or ethyl group. Preferable substituents on 16-position may be, for instance, one or more lower alkyl group(s) such as methyl or ethyl group, hydroxyl group(s), halogen atom(s) such as a chlorine atom or a fluorine atom and the like. Preferable substituent(s) on 20-position may be, for instance, saturated or unsaturated alkyl group(s), especially $C_1$-$C_4$ alkyl group(s), $C_1$-$C_4$ alkyl group(s) having alkoxy group(s) or alkoxy substituent(s) and the like.

The carbon atom of 6-position may constitutes a carbonyl group, and the configuration with respect to the carbon atom of 11-position may be $\alpha$, $\beta$ or mixture thereof.

Compounds having one or two lower alkyl group(s) such as methyl, ethyl and the like is preferable because of its high activity of tracheobronchodilation.

Further, compounds having a shorter $\omega$-chain (compounds in which the number of carbon atoms of $\omega$-chain is less than 8) and an alkoxy group, a phenoxy group, a phenyl group or others on the terminal position of the $\omega$-chain are also useful.

The PGEs of the present invention may include any isomers of the aboves, for instance, tautomers between the hydroxyl group at 11-position and the carbonyl group at 15-position, optical isomers, or geometric isomers and the like.

The tautomers between the hydroxyl group at 11-position and the carbonyl group at 15-position can be more easily formed when 15-keto-PGEs have an electron withdrawing group such as a fluorine atom at 16-position.

The equilibrium mixture of isomers, for instance, racemic mixture, tautomers of hydroxyl compounds and hemiacetals, also exhibits an activity similar to a single (not isomeric) compound thereof.

Examples of the typical compounds of the present Invention are: .

15-keto-PGE and 13,14-keto-dihydro-15-keto-PGE and their derivatives such as 6-keto-derivatives, $\Delta^2$-derivatives, 3R,S-methyl-derivatives, 16R,S-methyl-derivatives, 16,16-dimethyl-derivatives, 16R,S-fluoro-derivatives, 16,16-difluoro-derivatives, 17S-methyl-derivatives, 19-methyl-derivatives, and 20-methyl-derivatives.

In the present specification PGEs are named based on a prostanoic acid skeleton, but it can be named according to IUPAC nomenclature, according to which, for instance, PGE$_1$, is nominated as 7-{(1R,2R,3R)-3-hydroxy-2-[(E)-(3S)-3-hydroxy-1-octenyl]-5-oxo-cyclopentyl}-heptanoic acid; PGE$_2$ is nominated as (z)-7-{(1R,2R,3R)-3-hydroxy-2-[(E)-(3S)-3-hydroxy-1-octenyl]-5-oxo-cyclopentyl}-hept-5-enoic acid; 13,14-dihydro-15-keto-16R,S-fluoro-PGE$_2$ is nominated as (z)-7-{(1R,2R,3R)-3-hydroxy-2-[(4R,S)-4-fluoro-3-oxo-1-octyl]-5-oxo-cyclopentyl}-hept-5-enoic acid; 13,14-dihydro-15-keto-20-ethyl-11-dehydroxy-11R-methyl PGE$_2$ methyl ester is nominated as methyl 7-{(1R,2S,3R)-3-methyl-2-[3-oxo-1-decyl]-5-oxo-cyclopentyl}-hept-5-enoate; and 13,14-dihydro-6,15-diketo-19-methyl-PGE$_1$ ethyl ester is nominated as ethyl 7-{(1R,2R,3R)-3-hydroxy-2-(7-methyl-3-oxo-1-octyl)-5-oxo-cyclopentyl}-6-oxo-heptanoate.

The 15-keto-PGEs used in this invention may be prepared, for example, by the method noted in Japanese Patent Application No. 18326/1988. The disclosure on it is incorporated into the present specification.

A practical preparation of the 13,14-dihydro-15-keto PGEs involves the following steps; as shown in the synthetic charts (I) to (III), reaction of the aldehyde (2) prepared by the Collins oxidation of commercially available (−)-Corey lactone (1) with dimethyl (2-oxoheptyl)phosphate anion to give α,β-unsaturated ketone (3), reaction of the α,β-unsaturated ketone (3) to the corresponding saturated ketone (4), protection of the carbonyl group of the ketone (4) with a diol to the corresponding ketal (5), and deprotection of the p-phenylbenzoyl group to give the corresponding alcohol (6) followed by protection of the newly derived hydroxy group with dihydropyrane to give the corresponding tetrahydropyranyl ether (7). According to the above process, a precursor of PGEs of which ω-chain is a 13,14-dihydro-15-keto-alkyl group is prepared.

Using the above tetrahydropyranyl ether (7), 6-keto-PGE$_1$s (15) of which a group constituted with carbon atoms of 5-, 6- and 7-positions is

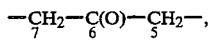

may be prepared in the following steps; reduction of the tetrahydropyranyl ether (7) with, for example, diisobutyl aluminum hydride to give the corresponding lactol (8), reaction of the lactol (8), with the yield generated from (4-carboxybutyl)triphenyl phosphonium bromide followed by esterification (10), cyclization between the 5,6-double bond and the hydroxyl group at 9-position with NBS or iodine to give the halogenated compound (11), dehydrohalogenation of the compound (11) with, for example, DBU to give the 6-keto compound (13) followed by Jones oxidation and removal of the protecting groups.

Furthermore, PGE$_2$s (19) of which a group constituted with carbon atoms of 5-, 6- and 7-position is

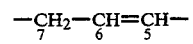

may be prepared in the following steps; as shown in the synthetic chart II, reduction of the above the tetrahydropyranyl ether (7) to give the lactol (8), reaction of the resultant lactol (8) with the ylide derived from (4-carboxybutyl)triphenyl phosphonium bromide to give the carboxylic acid (16) followed by esterification to give ester (17), Jones oxidation of the esters (17) to give the compound (18), and removal of the protecting groups.

Using the above the tetrahydropyranyl ether (7) as starting material, the compound having

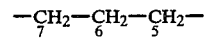

may be prepared by using the same process for preparing PGE$_2$s having

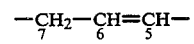

and applying the resultant compound (18) to catalytic reduction for reducing the double bond between the 5- and 6-positions followed by removal of the protection groups.

Synthesis of 5,6-dehydro-PGE$_2$s having

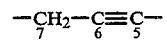

may be carried out by alkylation of the resulting a copper enolate derived after 1,4-addition of a monoalkylcopper complex or a dialkylcopper complex of the following formula:

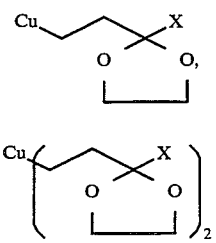

to 4R-t-butyldimethylsilyloxy-2-cyclopenten-1-one with 6-alkoxycarbonyl-1-iodo-2-hexyne or the derivatives.

The 11-β type PGEs can be prepared according to the synthetic chart III.

11-Dehydroxy-11-methyl-PGEs were obtained by reacting PGAs obtained by Jones oxidation of the hydroxy group at the C-9 position of the 11-tosylate with a dimethyl copper complex. Alternatively, PGAs may be prepared by converting an alcohol obtained after elimination of p-phenylbenzoyl group to a tosylate; treating the tosylate with DBU to give an unsaturated lactone, which is then converted, to a lactol; introducing an α-chain using Wittig reaction; and oxidizing the resulting alcohol (C-9 position).

11-Dehydroxy-11-hydroxymethyl-PGE can be obtained by a benzophenone-sensitized photoaddition of methanol to PGA.

The 15-keto-PGEs of this invention may be used as a medicine for animals and human beings and usually applied systemically or locally by the method of oral administration, oral administration by spraying, intravenous injection (including instillation), subcutaneous injection, suppository, spraying, coating, gargling and the like. Dose is determined depending on the animal to be treated, the human patient, age, body weight, symptom, therapeutic effect, administration route, treating time and the like, but is preferably 0.001-500 mg/kg.

As solid composition of this invention for oral administration, tablets, troches, capsules, pills, powders, granules and the like are included. The solid composition containing one or more active substances is mixed with at least an inactive diluent such as lactose, mannitol, glucose, hydroxypropyl cellulose, fine crystalline cellulose, starch, polyvinyl pyrolidone, magnesium aluminate metasilicate. The composition may contain additives other than the inactive diluent, such as lubricants (e.g. magnesium stearae), a disintegrator (e.g. cellulose calcium gluconates), stabilizers (e.g. $\alpha$-, $\beta$- or $\gamma$-cyclodextrins, etherated cyclodextrins (e.g. dimethyl-$\alpha$-, dimethyl-$\beta$-, trimethyl-$\beta$- or hydroxypropyl-$\beta$-cyclodextrins), branched cyclodextrins (e.g. glucosyl- or maltosyl-cyclodextrins), formyl cyclodextrins, sulfur-containing cyclodextrins, misoprotols or phospholipids. Such cyclodextrins may form an inclusion compound with 15-keto-PGEs in some cases to increase the stability of the compounds. The stability may be often increased by forming lyposome with phospholipids. Tablets and pills may be coated with an enteric or gastroenteric film such as white sugar, gelatin, hydroxypropylcellulose, hydroxypropylmethylcellulose phthalates and the like, if necessary, and furthermore they may be covered with two or more layers. Additionally, the composition may be in the form of capsules made of substance easily adsorbed such as gelatin.

Liquid compositions for oral administration include pharmaceutically acceptable emulsions, solutions, suspensions, syrups, elixirs and the like and contain a generally used inactive diluent such as purified water or ethyl alcohol. The composition may contain additives such as wetting agents, suspending agents, adhesives (e.g. saponins), sweeteners, flavors, perfumes and preservatives.

The compositions for oral administration may contain one or more active substance.

The composition of the present invention may be sprays which can be prepared according to a well known method. The sprays are particularly suitable for the prevention or treatment of paroxysm of asthema, which may be prepared, for instance, by dispersing effective compounds with the aid of surface active agent into blowing agents such as Flon.

The injection of this invention for non-oral administration includes sterile aqueous or nonaqueous solutions, suspensions, and emulsions. Diluents for the aqueous solution or suspension include, for example, distilled water for injection, physiological saline and Ringer's solution. Diluents for the nonaqueous solution and suspension include, for example, propylene glycol, polyethylene glycol, vegetable oils such as olive oil, alcohols such as ethanol and polysorbates. The composition may contain other additives such as preservatives, wetting agents, emulsifying agents, dispersing agents and the like. These are sterilized by filtration through, e.g. a bacteria-retaining filter, compounding with a sterilizer, gas sterilization or radiation sterilization. These can be prepared by producing a sterilized water or a sterilized solvent for injection before use.

Further, in case that the drugs must be rapidly absorbed such as in asthema the tracheobronchodilator of the present invention may be formulated to a sublingual tablet, which may be prepared by mixing or dissolving the effective components with carriers such as glycerin, lactose, mannitol, sorbitol and the like.

The tracheobronchodilator of the present invention may be formulated to a collutorium.

The 15-keto-PGEs of the present invention are effective to diseases with increase of airway resistance such as bronchial asthematics, infectious asthematic bronchitis, chronic bronchitis and the like.

EXAMPLE 1

Tracheaectasy

A male guinea pig weighing about 300 g was beaten to death, and immediately drew the blood by cutting its arteriae femoral as pouring water. A trachea was picked out and cut lengthwise at the opposite side of tracheal smooth muscle and cut into circular slices between cartilages. The obtained seven circular slices of the trachea were tied like as a chain with a thread, and hung into Magnus tube.

After the circular slices of trachea were held for 60-90 minutes until it became stable (disappearence of convulsion), they were administered with $5.4 \times 10^{-4}$M of histamin to be contracted. After the contraction reached to maximum, each test drug was cumulatively administered so as to inhibit the contraction caused by the histamin. The concentration of administered drug exhibiting the inhibition rates of 20% and 50% are represented by $IC_{20}$ and $IC_{50}$ respectively. The results are shown in Table 1.

TABLE 1

| Test drugs | $IC_{20}$ (M) | $IC_{50}$ (M) |
| --- | --- | --- |
| 1 | $8 \times 10^{-7}$ | $7 \times 10^{-6}$ |
| 2 | $2 \times 10^{-6}$ | $6 \times 10^{-6}$ |
| 3 | $9 \times 10^{-6}$ | — |
| 4 | $6 \times 10^{-6}$ | — |
| 5 | $4 \times 10^{-6}$ | $1 \times 10^{-5}$ |
| 6 | $1 \times 10^{-6}$ | $5 \times 10^{-6}$ |
| 7 | $3 \times 10^{-6}$ | — |
| 8 | $5 \times 10^{-6}$ | $2 \times 10^{-5}$ |
| 9 | $1 \times 10^{-7}$ | $4 \times 10^{-7}$ |
| 10 | $1 \times 10^{-7}$ | $6 \times 10^{-7}$ |
| 11 | $8 \times 10^{-7}$ | $4 \times 10^{-6}$ |
| 12 | $6 \times 10^{-7}$ | $3 \times 10^{-6}$ |
| 13 | $1 \times 10^{-6}$ | $3 \times 10^{-5}$ |
| 14 | $9 \times 10^{-7}$ | $3 \times 10^{-5}$ |
| 15 | $5 \times 10^{-7}$ | $4 \times 10^{-6}$ |
| 16 | $5 \times 10^{-6}$ | $4 \times 10^{-5}$ |
| 17 | $3 \times 10^{-6}$ | $1 \times 10^{-5}$ |
| 18 | $1 \times 10^{-6}$ | $1 \times 10^{-5}$ |
| 19 | $1 \times 10^{-6}$ | $5 \times 10^{-6}$ |
| 20 | $6 \times 10^{-7}$ | $2 \times 10^{-6}$ |
| 21 | $4 \times 10^{-7}$ | $2 \times 10^{-6}$ |
| 22 | $2 \times 10^{-6}$ | $8 \times 10^{-6}$ |
| 23 | $5 \times 10^{-7}$ | $2 \times 10^{-6}$ |
| 24 | $2 \times 10^{-6}$ | $1 \times 10^{-5}$ |
| 25 | $4 \times 10^{-5}$ | — |
| 26 | $1 \times 10^{-6}$ | $7 \times 10^{-6}$ |
| 27 | $8 \times 10^{-8}$ | $4 \times 10^{-7}$ |
| 28 | $7 \times 10^{-7}$ | $7 \times 10^{-6}$ |
| 29 | $6 \times 10^{-7}$ | $7 \times 10^{-6}$ |
| 30 | $6 \times 10^{-7}$ | $2 \times 10^{-6}$ |
| 31 | $4 \times 10^{-7}$ | $2 \times 10^{-6}$ |
| 32 | $1 \times 10^{-6}$ | $3 \times 10^{-5}$ |
| 33 | $1 \times 10^{-6}$ | $7 \times 10^{-6}$ |
| 34 | $3 \times 10^{-6}$ | $1 \times 10^{-5}$ |
| 35 | $9 \times 10^{-7}$ | $2 \times 10^{-5}$ |
| 36 | $5 \times 10^{-7}$ | $5 \times 10^{-6}$ |

TABLE 1-continued

| Test drugs | IC$_{20}$ (M) | IC$_{50}$ (M) |
|---|---|---|
| 37 | $4 \times 10^{-7}$ | $8 \times 10^{-6}$ |
| 38 | $6 \times 10^{-7}$ | $7 \times 10^{-6}$ |
| 39 | $3 \times 10^{-6}$ | $6 \times 10^{-5}$ |
| 40 | $2 \times 10^{-6}$ | $4 \times 10^{-5}$ |
| 41 | $4 \times 10^{-6}$ | — |
| 42 | $1 \times 10^{-5}$ | — |
| 43 | $1 \times 10^{-5}$ | — |
| 44 | $1 \times 10^{-5}$ | — |
| 45 | $2 \times 10^{-6}$ | $1 \times 10^{-5}$ |
| 46 | $1 \times 10^{-5}$ | — |
| 47 | $6 \times 10^{-7}$ | $3 \times 10^{-6}$ |
| 48 | $1 \times 10^{-5}$ | — |
| 49 | $7 \times 10^{-6}$ | — |
| 50 | $2 \times 10^{-5}$ | — |
| 51 | $1 \times 10^{-6}$ | $1 \times 10^{-5}$ |
| 52 | $1 \times 10^{-6}$ | — |
| 53 | $1 \times 10^{-5}$ | — |
| 54 | $8 \times 10^{-6}$ | $3 \times 10^{-5}$ |
| 55 | $2 \times 10^{-6}$ | $1 \times 10^{-5}$ |
| 56 | $2 \times 10^{-9}$ | $8 \times 10^{-8}$ |
| 57 | $1 \times 10^{-8}$ | $1 \times 10^{-7}$ |
| 58 | $1 \times 10^{-6}$ | $3 \times 10^{-5}$ |
| 59 | $1 \times 10^{-6}$ | $4 \times 10^{-6}$ |
| 60 | $3 \times 10^{-6}$ | $7 \times 10^{-6}$ |
| 61 | $7 \times 10^{-7}$ | $2.5 \times 10^{-6}$ |
| 62 | $4 \times 10^{-6}$ | — |
| 63 | $1 \times 10^{-5}$ | — |
| 64 | $3 \times 10^{-7}$ | $1 \times 10^{-6}$ |

| | Test Drugs |
|---|---|
| 1. | 13,14-dihydro-15-keto-PGE$_1$ |
| 2. | 13,14-dihydro-15-keto-PGE$_1$ ethyl ester |
| 3. | 13,14-dihydro-15-keto-$\Delta^2$-PGE$_1$ |
| 4. | 13,14-dihydro-15-keto-$\Delta^2$-PGE$_1$ methyl ester |
| 5. | 13,14-dihydro-6,15-diketo-PGE$_1$ methyl ester |
| 6. | 13,14-dihydro-6,15-diketo-PGE$_1$ ethyl ester |
| 7. | ($\pm$)13,14-dihydro-6,15-diketo-PGE$_1$ ethyl ester |
| 8. | 13,14-dihydro-6,15-diketo-PGE$_1$ n-butyl ester |
| 9. | 13,14-dihydro-6,15-diketo-16R,S-methyl-PGE$_1$ methyl ester |
| 10. | 13,14-dihydro-6,15-diketo-16R,S-methyl-PGE$_1$ ethyl ester |
| 11. | 13,14-dihydro-6,15-diketo-16,16-dimethyl-PGE$_1$ ethyl ester |
| 12. | 13,14-dihydro-6,15-diketo-16R,S-fluoro-PGE$_1$ ethyl ester |
| 13. | 13,14-dihydro-6,15-diketo-19-methyl-PGE$_1$ methyl ester |
| 14. | 13,14-dihydro-6,15-diketo-19-methyl-PGEI ethyl ester |
| 15. | 13,14-dihydro-6,15-diketo-20-methyl-PGE$_1$ ethyl ester |
| 16. | 13,14-dihydro-15-keto-PGE$_2$ |
| 17. | 13,14-dihydro-15-keto-PGE$_2$ methyl ester |
| 18. | 13,14-dihydro-15-keto-PGE$_2$ ethyl ester |
| 19. | 13,14-dihydro-15-keto-PGE$_2$ n-propyl ester |
| 20. | 13,14-dihydro-15-keto-PGE$_2$ n-butyl ester |
| 21. | 13,14-dihydro-15-keto-PGE$_2$ benzyl ester |
| 22. | 13,14-dihydro-15-keto-PGE$_2$ hydroxyethyl ester |
| 23. | 13,14-dihydro-15-keto-PGE$_2$ isopropyl ester |
| 24. | 13,14-dihydro-15-keto-$\Delta^2$-PGE$_2$ methyl ester |
| 25. | 13,14-dihydro-15-keto-3R,S-methyl-PGE$_2$ methyl ester |
| 26. | 13,14-dihydro-15-keto-3R,S-methyl-PGE$_2$ ethyl ester |
| 27. | 13,14-dihydro-15-keto-16R,S-methyl-PGE$_2$ methyl ester |
| 28. | 13,14-dihydro-15-keto-16R,S-methyl-PGE$_2$ ethyl ester |
| 29. | 13,14-dihydro-15-keto-3R,S-16R,S-dimethyl-PGE$_2$ methyl ester |
| 30. | 13,14-dihydro-15-keto-16,16-dimethyl-PGE$_2$ methyl eser |
| 31. | 13,14-dihydro-15-keto-16,16-dimethyl-PGE$_2$ ethyl ester |
| 32. | 13,14-dihydro-15-keto-16R,S-hydroxy-PGE$_2$ ethyl ester |

-continued

| | Test Drugs |
|---|---|
| 33. | 13,14-dihydro-15-keto-16R,S-fluoro-PGE$_2$ |
| 34. | 13,14-dihydro-15-keto-16R,S-fluoro-PGE$_2$ methyl ester |
| 35. | 13,14-dihydro-15-keto-16R,S-fluoro-PGE$_2$ ethyl ester |
| 36. | 13,14-dihydro-15-keto-16R,S-fluoro-20-methyl-PGE$_2$ methyl ester |
| 37. | 13,14-dihydro-15-keto-16R,S-fluoro-11-dehydroxy-11R-ethyl-PGE$_2$ ethyl ester |
| 38. | 13,14-dihydro-15-keto-11-dehydroxy-11R-methyl-PGE$_2$ ethyl ester |
| 39. | 13,14-dihydro-15-keto-17S-methyl-PGE$_2$ methyl ester |
| 40. | 13,14-dihydro-15-keto-19-methyl-PGE$_2$ methyl ester |
| 41. | 13,14-dihydro-15-keto-19-methyl-PGE$_2$ ethyl ester |
| 42. | 13,14-dihydro-15-keto-20-methoxy-PGE$_2$ methyl ester |
| 43. | 13,14-dihydro-15-keto-20-methoxy-2-PGE$_2$ methyl ester |
| 44. | 13,14-dihydro-15-keto-3R,S-methyl-20-methoxy-PGE$_2$ methyl ester |
| 45. | 13,14-dihydro-15-keto-16,16-dimethyl-20-methoxy-PGE$_2$ methyl ester |
| 46. | 13,14-dihydro-15-keto-5,6-dehydro-20-methoxy-PGE$_2$ methyl ester |
| 47. | 13,14-dihydro-15-keto-18-methoxy-19,20-dinol-PGE$_2$ methyl ester |
| 48. | 13,14-dihydro-15-keto-20-isopropylidene-PGE$_2$ |
| 49. | 13,14-dihydro-15-keto-20-isopropylidene-PGE$_2$ methyl ester |
| 50. | 13,14-dihydro-15-keto-20-ethyl-PGE$_2$ methyl ester |
| 51. | 13,14-dihydro-15-keto-20-ethyl-PGE$_2$ ethyl ester |
| 52. | 13,14-dihydro-15-keto-20-ethyl-11-dehydroxy-11R-methyl-PGE$_2$ methyl ester |
| 53. | 13,14-dihydro-15-keto-20-n-propyl-PGE$_2$ methyl ester |
| 54. | 15-keto-PGE$_2$ |
| 55. | 15-keto-16R,S-fluoro-PGE$_2$ methyl ester |
| 56. | PGE$_1$ |
| 57. | PGE$_2$ |
| 58. | 13,14-dihydro-15-keto-17S-methyl-PGE$_2$ ethyl ester |
| 59. | 13,14-dihydro-15-keto-20-methyl-PGE$_1$ |
| 60. | 15-keto-16R,S-fluoro-PGE$_2$ |
| 61. | 15-keto-17S-methyl-PGE$_2$ ethyl ester |
| 62. | 13,14-dihydro-15-keto-16R,S-fluoro-PGE$_1$ |
| 63. | 13,14-dihydro-6,15-diketo-18-methyl-PGE$_1$ ethyl ester |
| 64. | 13,14-dihydro-15-keto-16R,S-methyl-PGE$_1$ methyl ester |

EXAMPLE 2

Stimuli of Trachea

The strength of stimuli to trachea of humans was evaluated by actual spraying inhalation.

Each test drug was dissolved with a small amount of ethyl alcohol, to which distilled water was added to prepare a solution containing test drug at a concentration of 10 μg/ml. Four panels (K, D, T and O) were sprayed into their throats with the each test solution at a rate of 2 ml/min using an ultrasonic inhaler (NE-U10B available from Omlon K.K.), and the strength of the stimuli was observed. The results were shown in Table 2.

TABLE 2

| test sample | K | D | T | O |
|---|---|---|---|---|
| PGE$_1$ (comparative) | ++ | + | + | ± |
| 13,14-dihydro-6,15-diketo-16R,S- | — | — | — | — |

TABLE 2-continued

| test sample | K | D | T | O |
|---|---|---|---|---|
| methyl-PGE$_1$ methyl ester | | | | |

—: no stimuli
±: slight stimuli
+: strong stimuli
++: very strong stimuli

EXAMPLE 3

Inhibition of Increase of Airway Resistance

A male guinea pig weighing 300–400 g was intraperitoneally anesthetized with urethane 1.5 g/kg. The test animal was cannulated through the trachea, and then bromopanchlonium was intravenously administered at 0.3 mg/kg to make the test animal inactivate. The animal was respired using a vespirater for a small animal. The airway resistance was recorded on a recorder using a bronchospasin transducer. The administration of the test drug was made through a cannula into the jugular vein. The histamin was administered three times of each 3 μg/kg at 30 minutes intervals, and the increase of the airway resistance was determined. After the determination the test drug was intervenously administered, and then 4th administration of histamin was done after one minute. The increase of airway resistance due to histamin before and after the administration of the test drug was determined, from which inhibition rate of the increase due to the test drug was evaluated. The results are shown in Table 4.

TABLE 4

| test sample | dose (μg/kg) | inhibition rate (%) |
|---|---|---|
| 13,14-dihydro-15-keto-16,16-difluoro-PGE$_2$ | 1 | 42 |
| | 3 | 100 |
| PGE$_2$ | 3 | 92 |

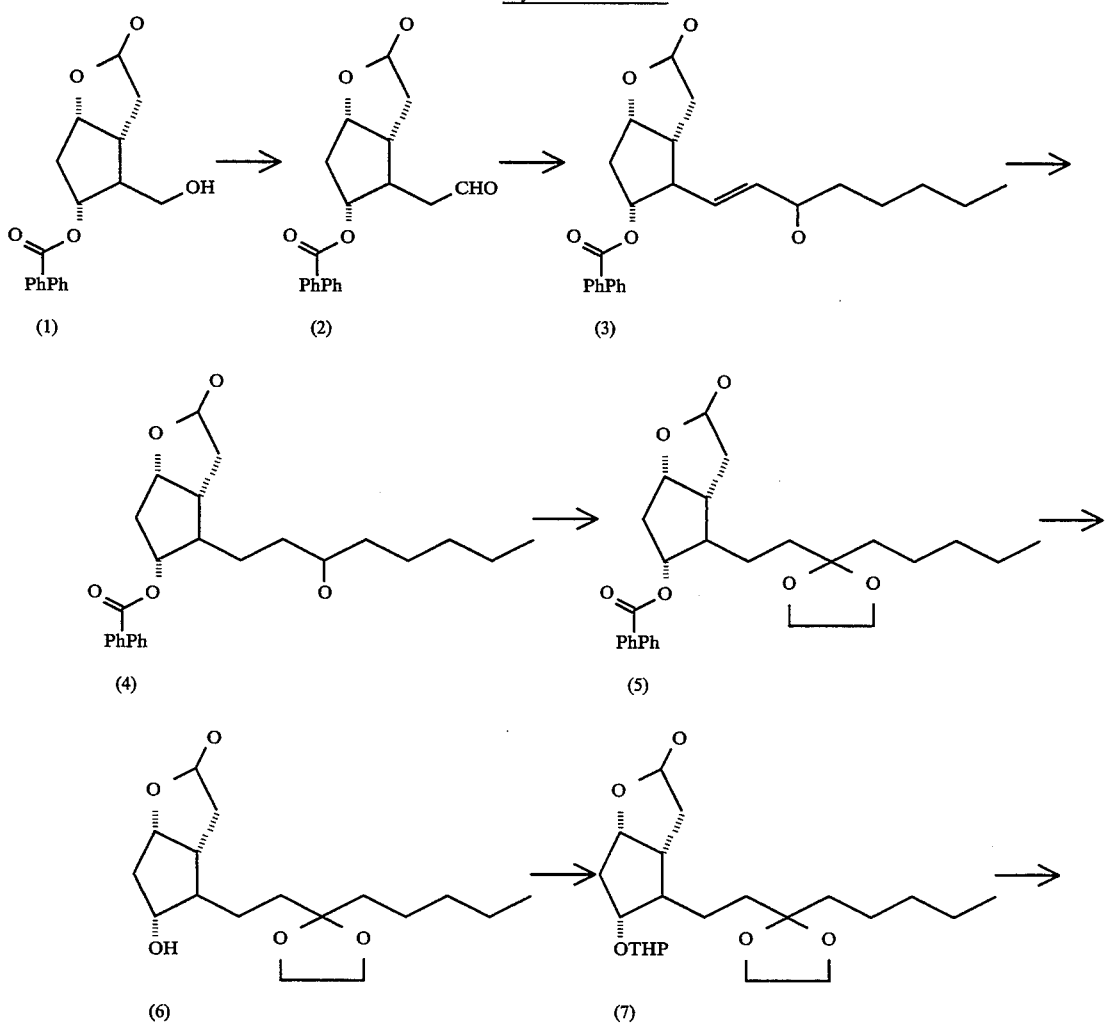

Synthetic Chart I

-continued
Synthetic Chart I
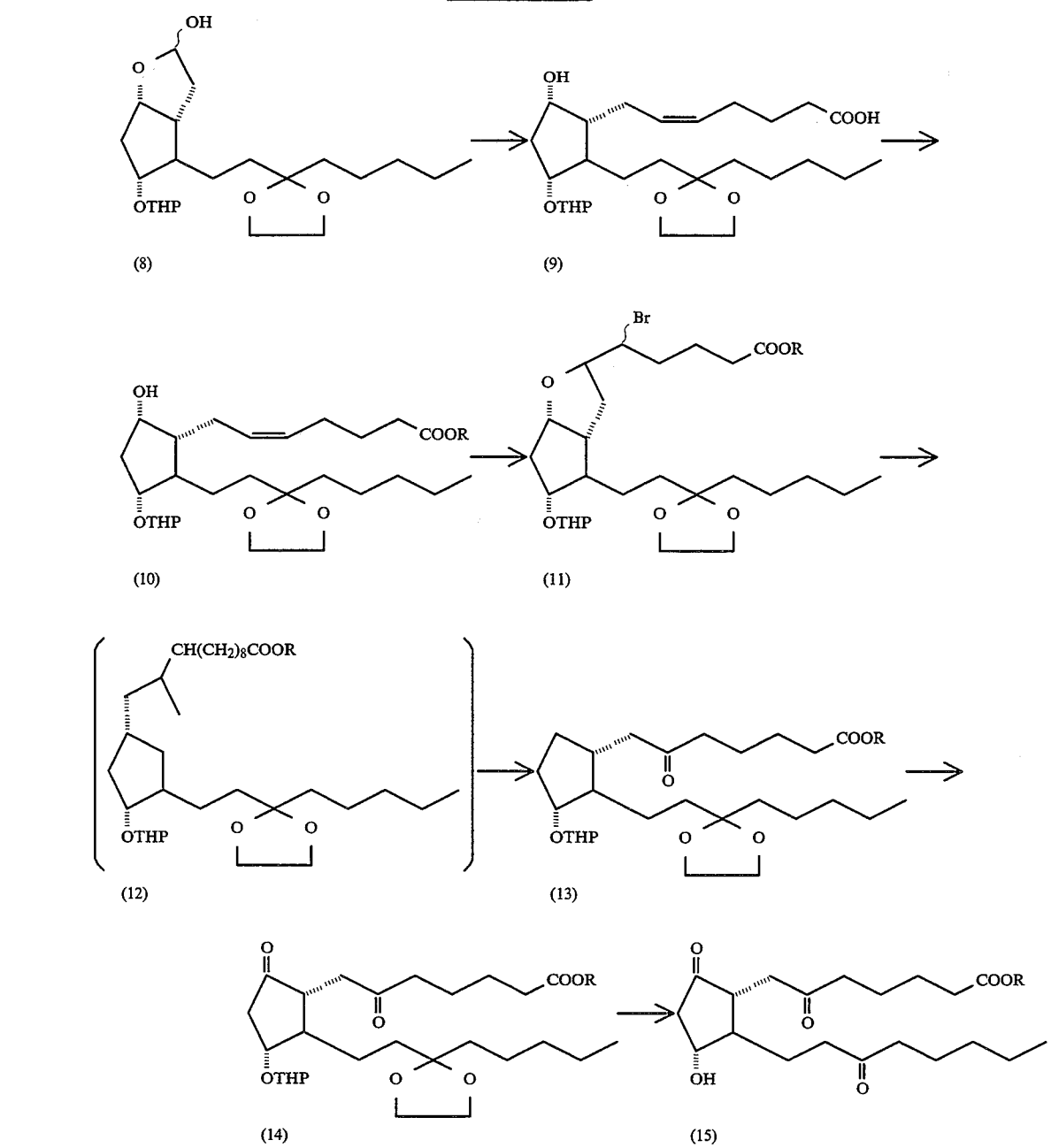
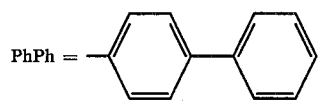
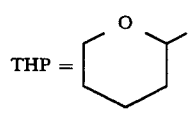
R:Et or Me

Synthetic Chart II
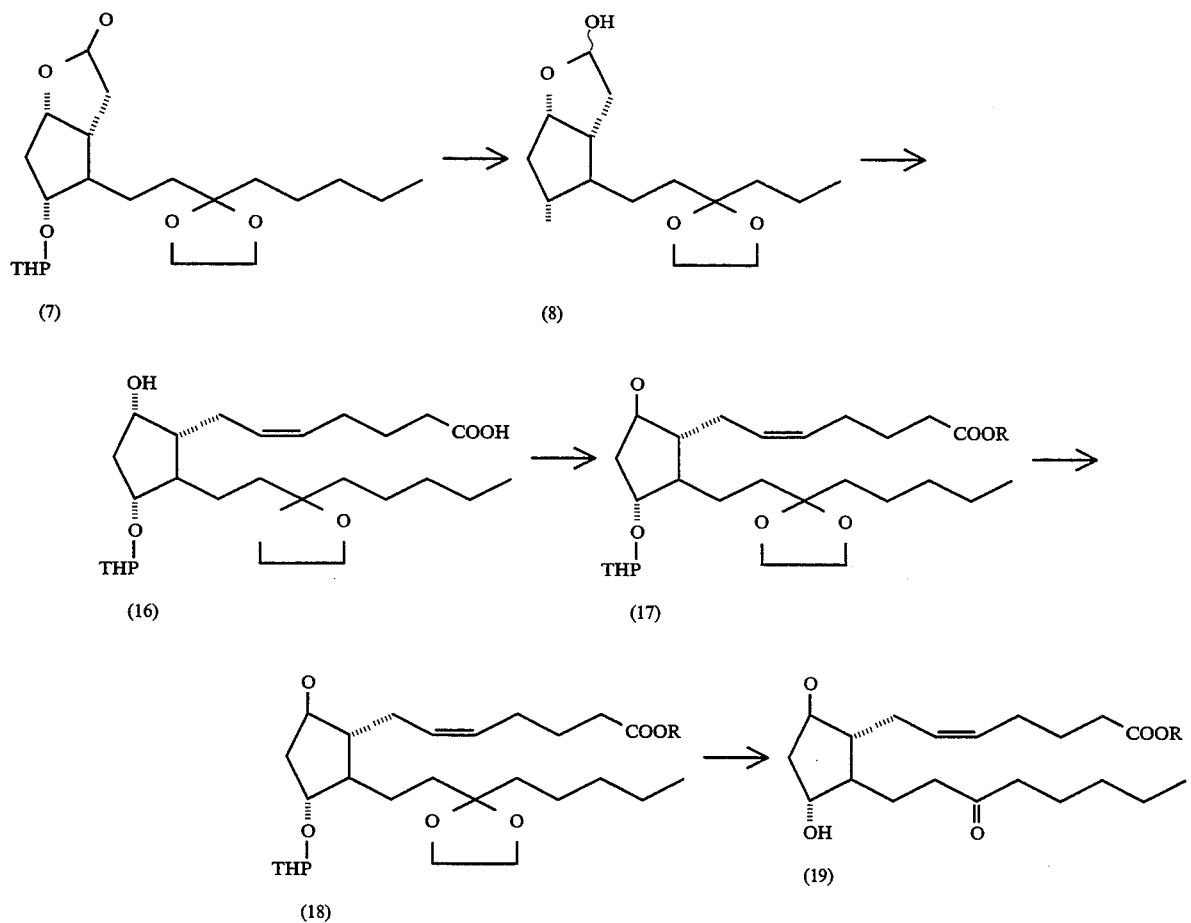
Synthetic Chart III
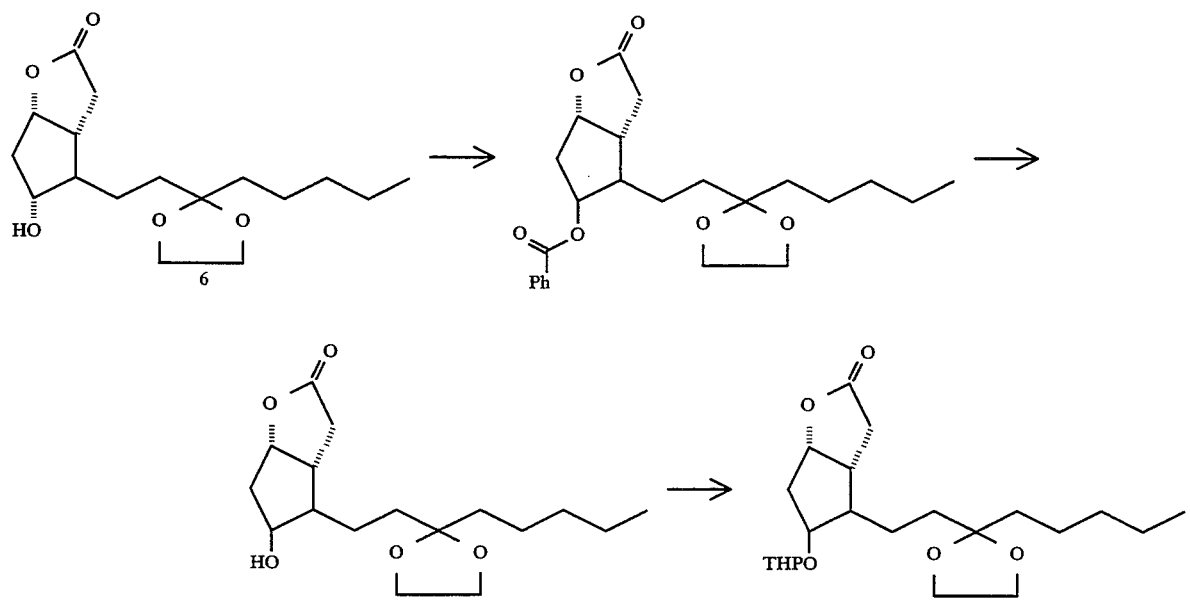

-continued
Synthetic Chart III

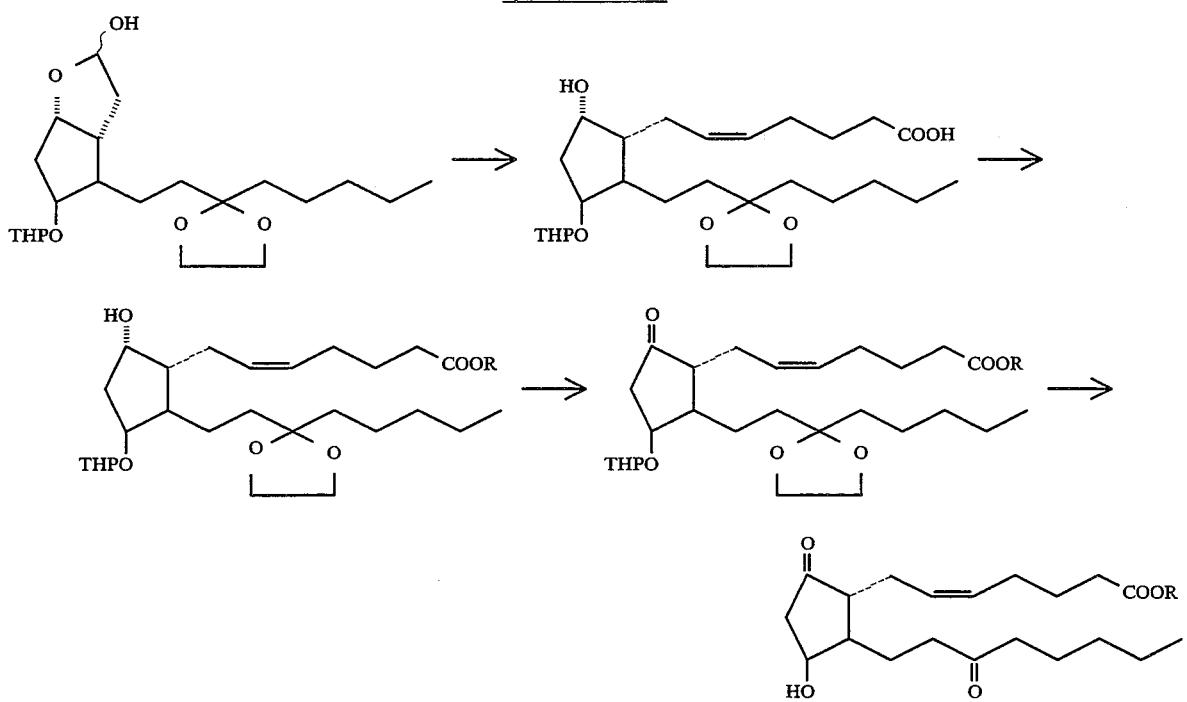

What is claimed is:

1. A method of dilating a tracheobronchea comprising administering to a patient in an amount effective for tracheobronchodilation a 15-keto-PGE represented by the following formula:

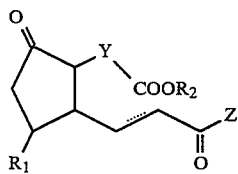

wherein $R_1$ is a hydroxyl group or a hydroxyalkyl group;

Y is a saturated or unsaturated hydrocarbon moiety having 2-6 carbon atoms wherein a portion of carbon atoms constituting the hydrocarbon moiety may be carbonyl or a portion of hydrogen atoms constituting the hydrocarbon moiety may be substituted by other atoms or groups;

Z is a saturated or an unsaturated hydrocarbon moiety constituting a straight chain having the carbon number of 1–10 which may be substituted with one or more other atom(s) or group(s), wherein at least a portion of hydrogen atoms of the hydrocarbon moiety is substituted by one or more halogen atom(s) or $C_1$–$C_2$ alkyl group(s) at the 16-position; and $R_2$ is a hydrogen atom, a physiologically acceptable salt or ester residue.

2. A method of treating conditions caused by the increase of airway resistance comprising administering to a patent an amount effective for tracheobronchodilation a 15-keto-PGE represented by the following formula:

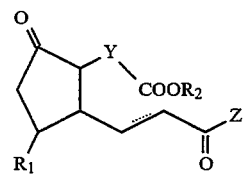

wherein $R_1$ is a hydroxyl group or a hydroalkyl group;

Y is a saturated or unsaturated hydrocarbon moiety having 2-6 carbon atoms wherein a portion of carbon atoms constituting the hydrocarbon moiety may be carbonyl or a portion of hydrogen atoms constituting the hydrocarbon moiety may be substituted by other atoms or groups;

Z is a saturated or an unsaturated hydrocarbon moiety constituting a straight chain having the carbon number 1–10 which may be substituted with one or more other atom(s) or group(s), wherein at least a portion of hydrogen atoms of the hydrocarbon moiety is substituted by one or two halogen atom(s) or $C_1$–$C_2$ alkyl group(s) at the 16-position; and $R_2$ is a hydrogen atom, a physiologically acceptable salt or ester residue.

3. A method for inducing tracheobronchial dilation comprising administering to a patient an effective amount of a 15-keto-16-substituted-PGE, in which the 15-keto-16-substituted-PGE is represented by the following formula:

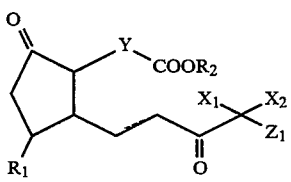

wherein $R_1$ is a hydroxyl group or a hydroxyalkyl group;

$X_1$ and $X_2$, each represents a hydrogen atom, a $C_1$-$C_2$ alkyl group or a halogen atom, provided that at least one of $X_1$ and $X_2$ is a $C_1$-$C_2$ alkyl group or a halogen atom;

Y is a saturated or unsaturated hydrocarbon moiety having 2–6 carbon atoms wherein a portion of carbon atoms constituting the hydrocarbon moiety may be carbonyl or a portion of hydrogen atoms constituting the hydrocarbon moiety may be substituted by other atoms or groups;

$Z_1$ is a saturated or unsaturated hydrocarbon moiety constituting a straight chain having the carbon number of 1–9 or a ring, wherein a portion of hydrogen atoms of the hydrocarbon moiety may be substituted by other atoms or groups;

$R_2$ is a hydrogen atom, a physiologically acceptable salt or ester residue.

4. A method for inducing tracheobronchial dilation comprising administering to a patient an effective amount of a 13,14-dihydro-15-keto-PGE, in which the 13,14-dihydro-15-keto-PGE is represented by the following formula:

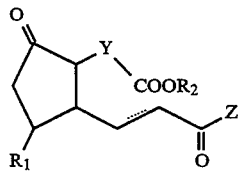

wherein $R_1$ is a hydroxyl group or a hydroxylalkyl group;

Y is a saturated or unsaturated hydrocarbon moiety having 2–6 carbon atoms wherein a portion of carbon atoms constituting the hydrocarbon moiety may be carbonyl or a portion of hydrogen atoms constituting the hydrocarbon moiety may be substituted by other atoms or groups;

Z is a saturated or an unsaturated hydrocarbon moiety constituting a straight chain having the carbon number of 1–10 which may be substituted with one or more other atom(s) or group(s), wherein at least a portion of hydrogen atoms of the hydrocarbon moiety is substituted by one or two halogen atom(s) or $C_1$-$C_2$ alkyl group(s) at the 16-position; and $R_2$ is a hydrogen atom, a physiologically acceptable salt or ester residue.

5. A method for inducing tracheobronchial dilation comprising administering to a patient an effective amount of a 15-keto-PGE, in which the 15-keto-PGE is represented by the following formula:

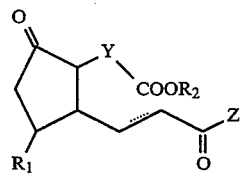

wherein $R_1$ is a hydroxyl group or a hydroxyalkyl group;

Y is a saturated or unsaturated hydrocarbon moiety having 2–6 carbon atoms wherein a portion of carbon atoms constituting the hydrocarbon moiety may be carbonyl or a portion of hydrogen atoms constituting the hydrocarbon moiety may be substituted by other atoms or groups;

Z is a saturated or an unsaturated hydrocarbon moiety constituting a straight chain having the carbon number of 1–10 which may be substituted with one or more other atom(s) or group(s), wherein at least a portion of hydrogen atoms of the hydrocarbon moiety is substituted by one or two halogen atom(s) or $C_1$-$C_2$ alkyl group(s) at the 16-position; and $R_2$ is a hydrogen atom, a physiologically acceptable salt or ester residue.

6. A method as in claim 5, in which a carbonyl group in the terminal position of the α-chain of the 15-keto-PGE is esterified.

7. A method as in claim 5, in which a bond between the 2-position and the 3-position of the 15-keto-PGE is a double bond.

8. A method as in claim 5, in which the 15-keto-PGE possesses a methyl group on the 3-position.

9. A method as in claim 5, in which the 15-keto-PGE is a 6,15-diketo-PGE.

10. A method as in claim 5, in which a hydrogen atom attached to the 20-position is substituted by a $C_1$-$C_4$ alkyl group or alkoxy group.

11. A method as in claim 5, in which one or two hydrogen atom(s) attached to the 16-position is (are) substituted by one or more alkyl group(s).

12. A method as in claim 11, in which the alkyl group is a methyl group.

13. A method as in claim 5, in which the 15-keto-PGE is a 15-keto-16-alkyl-PGE.

14. A method as in claim 5, in which the 15-keto-PGE is a -keto-16-methyl-PGE.

15. A method as in claim 5, in which the 15-keto-PGE is a 6,15-diketo-16-alkyl-PGE.

16. A method as in claim 5, in which the 15-keto-PGE is a 6,15-diketo-16-methyl-PGE.

17. A method as in claim 5, in which the 15-keto-PGE is a 13,14-dihydro-6,15-diketo-16-alkyl-PGE.

18. A method as in claim 5, in which the 15-keto-PGE is a 13,14-4-dihydro-6,5-diketo-16-methyl-PGE.

19. A method as in claim 5, in which $R_1$ is a hydroxyl group or a hydroxyalkyl group.

20. A method of claim 5, in which the conditions are bronchial asthematics, infectious asthematic bronchitis or chronic bronchitis.

21. A method of the claim 5, in which the administration is made by spraying, intravenous injection, subcutaneous injection, suppository coating or gargling.

* * * * *